United States Patent [19]

Morancais et al.

[11] Patent Number: 5,268,180

[45] Date of Patent: Dec. 7, 1993

[54] COSMETIC PHARMACEUTICAL OR FOODSTUFF COMPOSITION COMPRISING AN AQUEOUS DISPERSION OF LIPIDIC VESICLES

[75] Inventors: Jean-Luc Morancais, Ozoir-La-Ferriere; Michel Philippe, Antony, both of France

[73] Assignee: L'Oreal, Paris, France

[21] Appl. No.: 789,194

[22] Filed: Nov. 8, 1991

[30] Foreign Application Priority Data

Nov. 9, 1990 [FR] France .................................. 90 13917

[51] Int. Cl.$^5$ ............................................. A61K 9/127
[52] U.S. Cl. ...................................... 424/450; 424/401; 424/59; 424/63; 424/65; 424/70; 424/DIG. 4; 424/DIG. 13; 428/402.2; 514/827; 514/852; 514/864
[58] Field of Search ................. 424/450, 401, 420, 59, 424/63, 65, 70, DIG. 4, DIG. 13; 428/402.2; 514/827, 852, 864

[56] References Cited

FOREIGN PATENT DOCUMENTS

| | | |
|---|---|---|
| 0100382 | 2/1984 | European Pat. Off. . |
| 0180980 | 5/1986 | European Pat. Off. . |
| 0180980 | 5/1986 | European Pat. Off. . |
| 282449 | of 1986 | Japan . |
| 073938 | of 1989 | Japan . |
| 2177092 | of 1986 | United Kingdom . |
| 8810147 | 12/1988 | World Int. Prop. O. . |

OTHER PUBLICATIONS

Kiwada Chem. Pharm. Bull 33(2) 753, 1985.
Schenk et al, "Studies on sucrose-palmitate-stearate-containing vesicles encapsulating the cytostatic drug methylglyoxal-bis-quanyl-hydra-zone", Die Pharmazie, vol. 45, No. 10, Oct. 1990, pp. 747-749.
Derwent File Supplier WPIL (L), 1986 AN=-86-282499.
Derwent File Supplier WPIL (L), 1989 AN=-89-073938.
Kiwada et al, "Application of synthetic alkyl glycoside vesicles as drug carrier. I. Preparation and physical properties".
French Search Report of FR 90 13917.

*Primary Examiner*—Thurman K. Page
*Assistant Examiner*—G. S. Kishore
*Attorney, Agent, or Firm*—Cushman, Darby & Cushman

[57] ABSTRACT

This composition consists in an aqueous dispersion D, lamellar structure lipid vesicles encapsulating an aqueous phase E; it is characterised by the fact that the lipid phase forming the layers of the said vesicles is at least partly made up of a compound as formula (I):

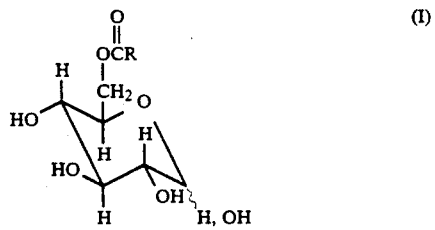

wherein R represents a linear saturated on unsaturated hydrocarbonated chain containing 9 to 17 carbon atoms. The compounds (I) have the advantage that they are easily biodegradable and of very low cytotoxicity.

18 Claims, No Drawings

COSMETIC PHARMACEUTICAL OR FOODSTUFF COMPOSITION COMPRISING AN AQUEOUS DISPERSION OF LIPIDIC VESICLES

This invention concerns a cosmetic, pharmaceutical or foodstuff compound comprising a dispersion of lipidic vesicles in an aqueous medium.

It is known that lipidic vesicles of these dispersions have a lamellar structure consisting of at least two lipidic layers arranged concentrically so as to define an enclosed volume; These vesicles encapsulate an aqueous phase which advantageously comprises active water-soluble substances such as, for instance of pharmaceutical, foodstuff or cosmetic nature, substance which are thus protected against external conditions. These vesicles may consist of ionic or non-ionic lipids.

Different families of surface agents are already known to form lipidic vesicle layers, Among these mention can be made of, for example, phospholipids, glycerolipids, polyglycerol ethers and quaternary ammonium compounds such as didodecyldimethylammonium bromide, also glucose ethers, such as hexadecyl glucopyrannosides, may also be employed in the formation of such vesicles. References can be made to the article entitled "Niosomes" by G. VANLERBERGHE et al., CNRS National Colloquia N.938, Bordeaux—1978, as well as the publication by H KIWADA et al. Chem Pharm. Bull. 33 (2) pp. 753–759, 1985.

The applicants have now found that a family of O-acylated derivatives (wherein the acyl group has 10–18 carbon atoms) in glucose position 6, of easily biodegradable nature and low cytotoxicity below that of alkyl glucopyrannosides, is also able to form lipidic vesicle layers in aqueous dispersions for use in cosmetic, pharmaceutical and foodstuff compositions. These glucose esters have never been suggested for use in such compositions. In the state of the art, reference has certainly been made to the use of hexose and fatty acid esters, of which the acyl group contains 7 to 10 carbon atoms, in the formulation of foaming compositions for use in cleaning, body hygiene and the foodstuff industry (International application WO 88/10147). However it was not clear that such glucose esters be employed in the formation of lipidic vesicles.

The object of this invention is a cosmetic, pharmaceutical or foodstuff composition having dispersed in aqueous medium D, lamellar structure lipidic vesicles encapsulating an aqueous phase E, characterized in that the lipidic phase forming the layers of the said vesicles consists at least of a compound of the following formula (I):

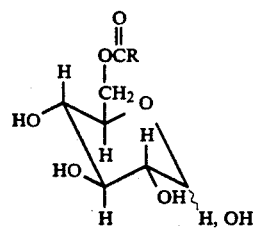

(I)

wherein R represents a linear, saturated or unsaturated hydrocarbon chain containing 9 to 17 carbon atoms.

Compounds according to formula (I) are known compounds. A process for their production is described below, and they are selected principally from those whose acyl residue, R—CO—, is a decanoyl, dodecanoyl, myristoyl, hexadecanoyl, stearoyl, oleoyl, linoleoyl or linolenoyl residue. As examples of compounds according to formula (I), mention can be made of $\alpha$-oleoyl-6-D-glucose, O-decanoyl-6-D-glucose, O-dodecanoyl-6-D-glucose, and O-hexadecanoyl-6-D-glucose. These compounds have the advantage of exhibiting a very low cytotoxicity and of being easily biodegradable with the release of glucose and an RCOOH acid.

The lipidic phase forming the vesicle layers may also enclose at least one complementary ionic and/or non-ionic amphiphile lipid of natural or synthetic origin, comprising at least one hydrophilic group selected from the group consisting of hydroxyl, ether oxide, carboxyl, phosphate and amine groups.

Complementary ionic amphiphile lipids may be selected from the group consisting of:
 natural phospholipids, such as soya or egg lecithin and sphingomyelin;
 synthetic phospholipids, such as dipalmitoylphosphatidylcholine or hydrogenated lecithins;
 amphoteric compounds, and
 anionic compounds.

Complementary non-ionic amphiphile lipids may be selected from the group consisting of:
(1) linear or branched polyglycerol ethers, of the following formula:

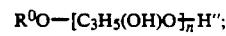

wherein:
 —$C_3H_5(OH)O$ is represented by the following structures taken jointly or separately;

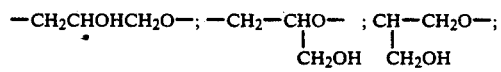

$\bar{n}$ is a mean statistical value between 1 and 6;
$R^0$ represents:
(a) an aliphatic, linear or branched, saturated or unsaturated chain having 12 to 30 carbon atoms; or lanolin alcohol hydrocarbon radicals; or residues of long chain diols;
(b) a residue, $R^1CO$, wherein $R^1$ is a $C_{11}$–$C_{17}$ aliphatic, linear or branched radical;
(c) a residue, $R_2$-[$OC_2H_3(R^3)$—], wherein:
 $R^2$ represents (a) or (b) defined above for $R^0$; wherein
 $OC_2H_3(R^3)$ is represented by the structures below taken jointly or separately:

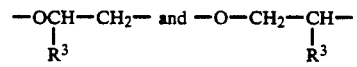

wherein $R^3$ represents (a) defined above for $R^0$.

(2) linear or branched polyglycerol ethers having two fatty chains;
(3) fatty polyoxyethylenated alcohols and sterols and polyoxyethylenated phytosterols;
(4) polyol ethers;
(5) polyol esters oxyethylenated or not;
(6) glycolipids of natural or synthetic origin;
(7) hydroxyamides having the formula:

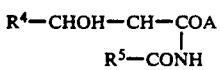

wherein:
$R^4$ is a $C_7$–$C_{21}$ alkyl or alkenyl radical;
$R_5$ a $C_7$–$C_{31}$ hydrocarbon radical, saturated or non-saturated;
COA is selected from the following two sets:
a residue having the formula

wherein:
B is a radical derived from mono- or polyhydroxylated primary or secondary amines; and
$R^6$ is a hydrogen atom or a methyl, ethyl or hydroxyethyl radical; and
a residue having the formula, —COOZ, wherein Z represents a $C_3$–$C_7$ polyol residue.

Lipidic vesicles of the composition according to the invention usually have an average diameter between 20 and 5000 nm.

The compositions according to the invention is prepared by all known means, for instance that described in French Patent 2 315 991. The process described in the said French Patent 2 315 991 involves bringing the lipid(s) destined to form the layers of the vesicles into contact with the aqueous phase for encapsulation in the said vesicles, allowing the lipids to swell in the said aqueous phase to form the lamellar phase; shaking to ensure mixing and to obtain a lamellar phase; then adding the dispersion liquid in a quantity exceeding that of the quantity of lamellar phase obtained and then shaking well.

The process described in European Patent application 90-4026481, may also be implemented, with a sequence of stages at least comprising dissolving a lipid in a non-water miscible organic solvent; adding the organic phase thus obtained to an aqueous phase; forming a dispersion of the two phases while vigorously shaking, the vesicle size being adjustable by varying the shaking speed while mixing the phases; ensuring evaporation of the solvent(s) while vigorously shaking; and, as required, concentrating the dispersion.

Furthermore in a known manner the lipid(s) forming the vesicles may be associated with at least one additive selected from the group consisting of:
long chain alcohols and diols
sterols, for instance cholesterol;
long chain amines and their quaternary ammonium derivatives;
hydroxyalkylamines, dihydroxyalkylamines; polyoxyethylenated fatty amines, long chain aminoalcohol esters and their salts and quaternary ammonium derivatives;
fatty alcohol phosphoric esters such as dicetylphosphate or its sodium salt;
alkyl sulphates such as sodium cetylsulphate;
certain polymers such as polypeptides and proteins, and
lipoprotides selected from mono- or polyacylated amino-acids or polypeptides, in which the residue, R'-CO-acyl, comprises a $C_{13}$–$C_{19}$ hydrocarbon chain, at least one function linking the polypeptide chain or amino-acid residue with the lipophile chain being an amide function, the carboxylic functions of the polypeptide chain or amino-acid residue being neutralized fully or partly with one or several alkaline cations, or an ammonium or substituted ammonium ion derived from an amine, the said lipoprotide(s) being present at the rate of 1% to 15% by weight relative to the total weight of the said lipids phase as such. These lipoprotides are described in French Patent 2 597 345.

The composition according to the invention advantageously contain 0.5 to 25% by weight of lipid(s) forming the vesicle layers, consisting of at least one formula (I) compound and, where necessary, admixed with at least one other compound as described above, the percentages being expressed by weight relative to the total weight of said composition.

According to a preferred embodiment described above, the aqueous phase E, encapsulated in the vesicles, is an aqueous solution of at least one active substance which is, preferably, relatively iso-osmotic compared with the aqueous phase D which surrounds the vesicles.

For a cosmetic composition according to the invention, the encapsulated aqueous phase E and/or dispersion D aqueous phase may each contain at least one water-soluble cosmetic substance selected from the group consisting of moisteners, artificial suntan compounds, skin colouring agents, skin solar protection agents, sun filters, anti-perspiration products, deodorants, astringents, freshening products, tonic products, wound-healing products, keratolytic products, depilatory products, perfumed lotions, water-soluble colorants, anti-dandruff agents, anti-seborrheic agents, oxidisers, reducers and extracts of animal or vegetable tissue.

In a pharmaceutical composition according to the invention, the aqueous phase E and/or aqueous phase D may also each contain at least one product selected from the group consisting of vitamins, hormones, enzymes, vaccines anti-inflammatories, antibiotics and bactericides.

In an invention variation, at least one non-water miscible liquid phase L is dispersed in aqueous phase D. In particular the composition according to the invention may contain 2% to 70% by weight of non-water miscible liquid phase L, relative to total weight of composition, the relative proportion by weight of lipids forming the vesicle(s) being between 0.02/1 and 10/1 of the dispersed liquid phase. In particular the component(s) of liquid phase L, dispersed in aqueous phase D, may each be selected from the group consisting of oils, such as fatty acid esters and polyols, and fatty acid esters and branched alcohols of the formula R7-COOR8, in which R7 represents the residue of high fatty acid containing 7 to 19 carbon atoms and R8 is a branched hydrocarbon chain having 3 to 20 carbon atoms; hydrocarbons, such as hexadecane, paraffin oil, perhydrosqualene; halogenated carbides such as perfluorodecahydronaphthalene; perfluorotributylamine; polysiloxanes, organic acid esters, ethers and polyethers. The liquid phase L may at least contain a perfume and/or an active liposoluble substance. Such liposoluble substances may consist of liposoluble solar filters, substances for improving dry or senile skins, tocopherol, vitamins E or F, vitamin A and its esters, retinoic acid, antioxidizers, essential fatty acids, glycyrrhetinic acid, keratolytic agents and carotenoids.

The aqueous phase D may also contain at least one additive selected from the group consisting of opacifiers, gelling compounds, perfumes, essences, antisolar filters and colorants.

This invention also concerns a foodstuff composition wherein the formula (I) lipid(s) and optional additive(s) forming the vesicle layers is/are edible lipids; that the aqueous phase E and aqueous phase D optionally contain at least one water-soluble vitamin and that the phase L component(s), if present, is/are selected from edible oils and optionally contain(s) at least a liposuble vitamin.

The following description is now given to provide a better understanding of the invention and for the sole purposes of illustration and non-restrictive information, and includes featuring several procedures.

Examples 1–4 describe the preparation of glucose esters of formula (I) and Examples 4 and 5 describe cosmetic compositions containing glucose esters employed to produce the lipid vesicles used in these cosmetic compositions.

The procedure to prepare O-acylated derivatives in position 6 of D-glucose is generally as follows: the synthesis is achieved on the basis of the selected acid chloride and D-glucose as described by REINEFELD et al, "Die Stärke", N.6, pp. 181–189, 1968:

72 g of D-glucose and 1 liter of pyridine are heated for 30 minutes at 70° C. in a 2 liter flask fitted with a stirrer and rising coolant with calcium chloride guard, until a colorless liquid solution is obtained. The reaction medium is cooled to room temperature, and then a solution of the required acid chloride (0.133 moles) is poured into 300 ml of tetrahydrofuran. The mixture is stirred for 15 hours at room temperature. The reaction is monitored by thin layer chromatography (MERCK 5719 silica gel plates); (using 15/85 methanol/dichloromethane as elutrient, and iodine as indicator). The mixture is taken up in a 93/7 mixture dichloromethane/methanol and then chromatographed a silica gel column (with 90/10 dichloromethane/methanol elutrient), and finally isolating the O-acyl-6-D-glucopyrannose (25% yield).

Cytotoxicity of said O-acyl-6-D-glucopyrannoses has been tested by in vitro inhibition procedure on V79 cell growth in Chinese hamster lung fibroblasts. Cells are prepared at the rate of 5000 cells/cm$^2$ using 96 cavity culture dishes. The central part of the culture contains 0.4% by weight of dimethylsulphoxide. After 24 hours of incubation, the cells were treated with increasing amounts of test glucopyrannose. Cell growth was assessed after treating with additions of total cell proteins for 3 days. The concentration in µg/ml, to inhibit cell growth by 50% was then determined ($CI_{50}$).

For comparison purposes, tests were carried out under the same conditions on glucopyrannoside 1 hexadecyl—(not included in compounds used according to the invention); a $CI_{50}$ value of 12 µg/ml was found.

EXAMPLE 1

Preparation of O-hexadecanoyl-6-D-glucose

Using hexadecanoyl chloride, 23 g of the cited product with a melting point of 145° C. were obtained, and subsequently recrystallised in acetonitrile.

The basic analysis of the product thus obtained gives the following results:

| Example 1 | C | H | O |
|---|---|---|---|
| Calculated for $C_{22}H_{42}O_7$ (MW = 418.6) | 63.13 | 10.11 | 26.76 |
| Determined | 63.42 | 10.18 | |

The nuclear magnetic resonance spectrum of the 13C ($C_5D_5N$) complies with the expected structure.

In the cytotoxicity study carried out as outlined above, the solubility limit of the product obtained did not allow tests beyond 30 µg/ml, which represents the $CI_{20}$ concentration at which cell inhibition is of the order of 20%.

EXAMPLE 2

Preparation of O-oleoyl-6-D-glucose

Using oleoyl chloride, 24 g of the relevant product were obtained having a melting point of 114° followed by recristallisation in isopropyl ether.

The basic analysis of the product thus obtained gives the results shown below:

| Example 2 | C | H | O |
|---|---|---|---|
| Calculated for $C_{24}H_{44}O_7$ 1H2O (MW = 462.6) | 62.31 | 10.02 | 27.67 |
| Determined: | 62.9 | 9.74 | |

The nuclear magnetic resonance spectrum of the 13C ($C_5D_5N$) complies with the expected structure.

The $CI_{50}$ cell growth inhibiting concentration, as defined above, was equal to 59.3 µg/ml.

EXAMPLE 3

Preparation of O-dodecanoyl-6-D-glucose

Using dodecanoyl chloride, 19.5 g of the relevant product were obtained having a melting point of 121° C., subsequently recrystallized in acetonitrile.

The basic analysis of the product thus obtained gives the results shown below:

| Example 3 | C | H | O |
|---|---|---|---|
| Calculated for $C_{18}H_{34}O_7$, 2H2O (MW = 398.5) | 54.25 | 9.61 | 36.13 |
| Determined | 53.72 | 9.28 | |

The nuclear magnetic resonance spectrum of the 13C ($C_5D_5N$) complies with the expected structure.

The $CI_{50}$ cell growth inhibiting concentration, as defined above, was equal to 29.0 µg/ml.

EXAMPLE 4

Preparation of O-dodecanoyl-6-D-glucose

Using dodecanoyl chloride, 18 g of the desired product were obtained having a melting point of 124° C. and was subsequently recrystallized in a mixture of isopropanol/water.

Basic analysis of the product obtained gives the results shown below:

| Example 4 | C | H | O |
|---|---|---|---|
| Calculated for C16H30O7 (MW = 334.4) | 57.47 | 9.04 | 33.49 |

| -continued | | | |
|---|---|---|---|
| Example 4 | C | H | O |
| Determined | 57.36 | 9.08 | |

The nuclear magnetic resonance spectrum of the 13C (deuterized dimethylsulphoxide) complies with the expected structure.

EXAMPLE 5

A composition of the following formulation was prepared:

| | |
|---|---|
| Example 2 compound | 38 g |
| Cholesterol | 38 g |
| Sodium dicetyl phosphate | 4 g |
| Preservative | 3 g |
| Anti-oxidation agent | 0.5 g |
| Water as required | 1000 g |

In a mixture of 400 ml of dichloromethane and 400 ml of methanol, quantities of 38 g of O-oleoyl-6-D-glucose, 38 g of cholesterol and 4 g of sodium dicetyl phosphate were dissolved. The resulting solution was gradually evaporated at progressively reduced pressure (660 to 13 mbars approx.) in a flask heated to 40° C.

An aqueous solution of 3 g of preservative, 0.5 g of anti-oxidation agent and 916.5 g of water were added to the resulting lipidic solution. The mixture was heated to 70° C. and shaken for 2 hours in a rig with oscillator arms.

A single topical application of 14 mg/cm² of the resulting fluid cream was then made to an area of previously cleaned dry skin. The application was repeated daily. It was found that the non-greasy cream had very good cosmetic properties owing to excellent spreading and rapid skin-penetrating characteristics.

EXAMPLE 6

A composition of the following formulation was prepared:

| | |
|---|---|
| Example 3 compound | 38 g |
| Cholesterol | 38 g |
| Sodium dicetyl phosphate | 4 g |
| Preservative | 3 g |
| Anti-oxidation agent | 0.5 g |
| Water as required | 1000 g |

The procedures of Example 5 were repeated. A single topical application of 15 mg/cm² was made of the resulting thick cream to an area of previously cleaned dry skin. The application was repeated daily. Owing to its excellent spreading and rapid skin-penetrating properties this non-greasy cream had very good cosmetic properties.

EXAMPLE 7

A composition having the following formulation was prepared:

| | |
|---|---|
| Example 1 compound | 1.75 g |
| Cholesterol | 2.0 g |
| Sodium dicetyl phosphate | 0.25 g. |
| Soya lecithin sold by FLUKA under the name "ASOLECTIN" | 1.00 g |
| Glycerol | 1.90 g. |
| Water as required | 100.00 |

In a mixture of 145 ml of dichloromethane and 115 ml of methanol, 1.76 g of O-hexadecanoyl-6-glucose, 2 g of cholesterol 0.25 g of sodium dicetyl phosphate and 1.0 g of soya lecithin are dissolved. The resulting solution was evaporated under gradually reduced pressure (approx. 660 to $13 \times 10^2$ pascals) in a rotating flask at 40° C.

An aqueous solution of 1.0 g glycerol and 93.1 g of water was then added to the lipidic film obtained. The oxygen was then removed by bubbling nitrogen through it and degassing in an ultrasonic container.

The mixture was heated to 45° C. and shaken for 2 hours in a rig with oscillating arms.

On return to ambient temperature, the dispersion was heated to 30° C. and then processed for 2 minutes with an ultrasonic homogenizer.

The resulting milk has the same properties as the cream in example 5, while also having a hydrating effect on the skin.

EXAMPLE 8

A composition having the following formulation was prepared:

| | |
|---|---|
| Example 1 compound | 1.25 g |
| Cholesterol | 2.30 g |
| Sodium dicetyl phosphate | 0.25 g |
| Non-ionic amphiphile lipid as in the formula $C_{16}H_{33}O\text{-}[C_3H_5(OHO)]$ | 1.13 g | wherein $-C_3H_5[OHO]_n-H$ is represented by the following structures taken jointly or separately:

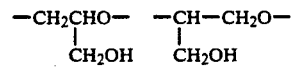

and $\bar{n}$ has an average statistical value equal to 3

| | |
|---|---|
| glycerol | 1.90 g |
| water as required | 100.00 g |

In a 16 ml dichloromethane and 40 ml methanol mixture, 1.25 g of O-hexadecanoyl 6-D-glucose, 2.3 g of cholesterol, 0.25 g of sodium dicetyl phosphate and 1.13 g of the above non-ionic amphiphile lipid 1.13 g were dissolved. The resulting solution was evaporated under gradually reduced pressure (approx. 660 to $13 \times 10^2$ pascals) in a rotating flask at 40° C.

An aqueous solution of 1.9 g of glycerol and 93.1 g of water was then added to the resulting lipidic film. The material was then deoxygenated by bubbling nitrogen through it and degassing it in an ultrasonic container.

The mixture was heated to 70° C. and shaken for 2 hours in a rig with oscillating arms.

On return to ambient temperature, the dispersion was heated to 30° C. and then processed for 2 minutes with an ultrasonic homogenizer.

The resulting milk has the same properties as the composition of example 7.

We claim:

1. A composition comprising, in an aqueous medium, a dispersion of lipid vesicles encapsulating an aqueous phase, said lipid vesicles having a lamellar structure comprising at least two lipidic concentrically arranged layers defining an enclosed volume so as to encapsulate said aqueous phase, and lipidic phase forming said layers comprising at least one compound having the formula

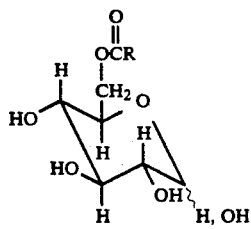
(I)

wherein
R represents a linear, saturated or unsaturated hydrocarbon chain containing 9 to 17 carbon atoms.

2. The composition of claim 1 wherein said lipidic phase is present in an amount ranging from 0.5 to 25 percent by weight based on the total weight of said composition.

3. The composition of claim 1 wherein the acyl R—CO-residue is selected from the group consisting of a decanoyl, dodecanoyl, myristoyl, hexadecanoyl, stearoyl, oleoyl, linoleoyl and linolenoyl residue.

4. The composition of claim 1 wherein said compound of formula I is selected from the group consisting of O-oleoyl-6-D-glucose, O-decanoyl-6-D-glucose, O-dodecanoyl-6-D-glucose and O-hexadecanoyl-6-D-glucose.

5. The composition of claim 1 wherein said lipidic phase forming said layers also includes an ionic amphiphilic lipid selected from the group consisting of a natural phospholipid, a synthetic phospholipid, an amphoteric compound and an anionic compound.

6. The composition of claim 1 wherein said lipidic phase forming said layers also includes another nonionic amphiphilic lipid selected from the group consisting of (1) a linear or branched chain polyglycerol ether having the formula

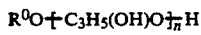

wherein
—C$_3$H$_5$(OH)O, jointly or separately represents —CH$_2$CHOHCH$_2$O—,

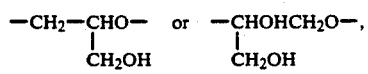

$\overline{n}$ has a statistical average value ranging from 1 to 6, R$^0$ represents
(a) an aliphatic, linear or branched, saturated or unsaturated chain containing 12 to 30 carbon atoms or a lanolin alcohol hydrocarbon chain, or the residue of a long chain diol,
(b) R$^1$CO wherein R$^1$ represents an aliphatic, linear or branched, radical having 11 to 17 carbon atoms,
(c)

wherein
R$^2$ represents (a) or (b) defined above for R$^0$ and wherein OC$_2$H$_3$(R$^3$) represents

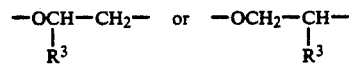

wherein R$^3$ represents (a) defined above for R$^0$,
(2) a linear or branched polyglycerol ether having two fatty chains,
(3) a fatty polyoxyethylenated alcohol, a fatty polyoxyethylenated sterol or a polyoxyethylenated phytosterol,
(4) a polyol ether,
(5) a polyol ester,
(6) an oxyethylenated polyol ester,
(7) a natural or synthetic glycolipid, and
(8) a hydroxyamide having the formula

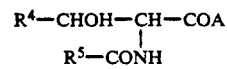

wherein
R$^4$ represents alkyl or alkenyl having 7 to 21 carbon atoms,
R$^5$ represents a saturated or unsaturated hydrocarbon radical having 7 to 31 carbon atoms,
COA represents a member selected from the group consisting of
(i)

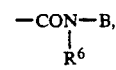

wherein B is a radical derived from a mono- or polyhydroxylated primary or secondary amine,
R$^6$ is hydrogen, methyl, ethyl or hydroxyethyl and
(ii) —COOZ wherein Z represents a polyol residue having 3-7 carbon atoms.

7. The composition of claim 1 wherein said lipidic phase forming said layers also contains at least one additive selected from the group consisting of a fatty alcohol, a fatty diol, a sterol, a fatty amine or a quaternary ammonium derivative thereof, a hydroxyalkylamine, a dihydroxyalkylamine, a polyoxyethylenated fatty amine, a fatty amino-alcohol ester or a salt thereof or a quaternary ammonium derivative thereof, a fatty alcohol phosphoric ester, an alkyl sulphate, a polypeptide polymer, a protein polymer, and a lipoprotide selected from a mono- or polyacylated amino acid, or a polypeptide derivative having an R'-CO-aryl residue wherein R' is a hydrocarbon chain containing 13-19 carbon atoms, and wherein at least one of the functions linking the polypeptide chain or amino-acid residue with the lipophile chain being an amide function and wherein at least a portion of the polypeptide chain or amino-acid residue carboxylic functions is neutralized by an alkaline cation or an ammonium ion.

8. The composition of claim 1 wherein the aqueous phase encapsulated in said vehicles is an aqueous solution of an active substance.

9. The composition of claim 1 wherein said aqueous medium in which said vesicles are dispersed or said aqueous phase encapsulated in said vesicles, or both, contain at least one water-soluble cosmetic substance selected from the group consisting of a moisturizer, a suntan compound, a skin coloring agent, a solar protection agent, an antiperspirant agent, a deodorant, an astringent, a freshening product, a tonic product, a wound-healing product, a keratolytic product, a depilatory, a perfumed lotion, a water-soluble colorant, an antidandruff agent, an antiseborrheic agent, an oxidizer and a reducing agent.

10. The composition of claim 1 wherein said aqueous medium in which said vesicles are dispersed or said aqueous phase encapsulated in said vesicles, or both, contain at least one pharmaceutical substance selected from a vitamin, a hormone, an enzyme, a vaccine, an anti-inflammatory agent, an antibiotic or a bactericide.

11. The composition of claim 1 wherein said lipidic phase forming said layers also contains at least one liposoluble active substance.

12. The composition of claim 11 wherein said liposoluble active substance is selected from a solar filter, an agent for improving dry skin, vitamin E or F, vitamin A or an ester thereof, retinoic acid, an antioxidant, an essential fatty acid, glycyrrhetinic acid, a keratolytic agent or a carotenoid.

13. The composition of claim 1 wherein said aqueous medium containing said vesicles dispersed therein also contains a dispersion of a water-insoluble liquid present in an amount ranging from 2 to 70 percent by weight based on the total weight of said composition and wherein the weight ratio of said lipid vesicles to said water-insoluble liquid dispersed in said aqueous medium ranges from 0.02/1 to 10/1.

14. The composition of claim 13 wherein said water-insoluble liquid is selected from a fatty acid ester having the formula $R^7$—$COOR^8$ wherein $R^7$ is a fatty acid residue containing 7 to 19 carbon atoms and $R^8$ is a branched hydrocarbon chain containing 3 to 20 carbon atoms; a hydrocarbon; paraffin oil; perhydrosqualene; perfluorodecahydro naphthalene; perfluoroributylamine; and a polysiloxane.

15. The composition of claim 13 wherein said water-insoluble liquid dispersed in said aqueous medium also contains a perfume or a liposoluble active substance, or both.

16. The composition of claim 1 wherein said aqueous medium in which said vesicles are dispersed also contains at least one additive selected from the group consisting of an opacifier, a gelling compound, an essence, a perfume, an anti-solar filter and a colorant.

17. The composition of claim 15 wherein said liposoluble active substance is selected from the group consisting of an anti-solar filter, a substance for improving the condition of dry skin and an antioxidant.

18. The composition of claim 13 wherein said lipidic phase forming said layers is an edible lipid, said aqueous phase encapsulated in said vesicles and said aqueous medium in which said vesicles are dispersed optionally contain at least one water-soluble vitamin, and said water-insoluble liquid dispersed in said aqueous medium contains an edible oil and optionally a liposoluble vitamin.

* * * * *